United States Patent [19]

Bakel

[11] 4,397,676
[45] Aug. 9, 1983

[54] N-PHOSPHONOMETHYLGLYCINE DERIVATIVES

[75] Inventor: Izhak Bakel, Ramat Gan, Israel

[73] Assignee: Geshuri Laboratories Ltd., Tel-Mond, Israel

[21] Appl. No.: 369,425

[22] Filed: Apr. 19, 1982

[30] Foreign Application Priority Data

Mar. 8, 1982 [IL] Israel ................................ 65187

[51] Int. Cl.³ .................... C07F 9/38; A01N 57/20
[52] U.S. Cl. ................................ 71/86; 260/501.12
[58] Field of Search .................. 260/501.12; 71/86

[56] References Cited

U.S. PATENT DOCUMENTS

| 3,835,000 | 9/1974 | Frazier et al. | 71/86 |
| 3,853,530 | 12/1974 | Franz | 260/501.12 |
| 3,969,398 | 7/1976 | Hershman | 260/502.5 F |
| 4,147,719 | 4/1979 | Franz | 260/502.5 F |

FOREIGN PATENT DOCUMENTS 1580688  7/1969  France ...................... 260/501.12

Primary Examiner—J. E. Evans
Attorney, Agent, or Firm—Cushman, Darby & Cushman

[57] ABSTRACT

The invention provides N-Phosphonomethylglycine derivatives of the general formula I

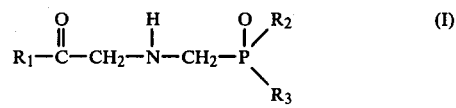

wherein $R_1$, $R_2$ and $R_3$ are independently selected from —OH and —$OR_4$ wherein $R_4$ is a salt forming cation iminourea derivative of the general formula II

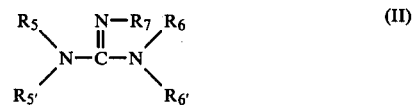

wherein $R_5$, $R_{5'}$, $R_6$, $R_{6'}$ and $R_7$ are independently

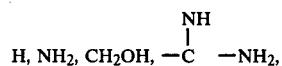

or an aryl, cycloalkyl or straight or branched chain alkyl or alkenyl group optionally substituted by hydroxy or halogen, or an alkylaryl group, provided that at least one but no more than two of $R_1$, $R_2$ or $R_3$ are $OR_4$; no more than two $R_5$, $R_{5'}$, $R_6$, $R_{6'}$ are aryl or substituted aryl; and no more than one of $R_5$, $R_{5'}$, $R_6$, $R_{6'}$ and $R_7$ is $CH_2OH$. The invention also provides a process for preparing the above N-Phosphonomethylglycine imino urea salts as well as providing phytotoxic compositions containing the same.

12 Claims, No Drawings

N-PHOSPHONOMETHYLGLYCINE DERIVATIVES

The present invention relates to N-phosphonomethylglycine (hereinafter referred to as NPMG) derivatives, methods for the production thereof and herbicidal compositions containing them. More specifically, the present invention relates to a whole class of newly discovered NPMG salts which surprisingly exhibit phytotoxic properties equal to and even superior to the most effective NPMG derivative marketed to date.

The compound NPMG is known for more than twenty years and it can be prepared as mentioned in U.S. Pat. No. 3,160,632 (1961) by the oxidation of the corresponding aminophosphinic compound utilizing mercuric chloride and other oxidizing agents.

NPMG in itself is a very effective phytotoxicant or herbicide, however, becasue it is relatively insoluble in water and conventional organic solvents, it is not as readily amenable to commercial formulation as are its derivatives. It is therefore generally preferred to utilize the more readily soluble derivatives of this compound in which at least one of the hydrogens in the hydroxy groups of NPMG has been replaced to form a water soluble salt.

In Israel Pat. No. 37993 there are described and claimed compounds of the formula:

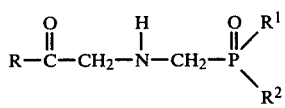

wherein R, $R^1$ and $R^2$ are independently selected from —OH and —$OR^6$, wherein $R^6$ is a salt-forming cation selected from the groups consisting of cations of alkali metals, alkaline earth metals, copper, zinc, manganese, nickel, ammonium and organic ammonium selected from primary-, secondary- and tertiary-alkyl, alkenyl and alkynylamines, none of these having more than two amine groups; primary aryl amines, primary aryl diamines and heterocyclic amines and the acid addition salts of strong acids of the above, wherein R, $R^1$ and $R^2$ are OH; provided that no more than two of R, $R^1$ and $R^2$ are —$OR^6$ when $R^6$ designates ammonium or organic ammonium (as above defined), and provided that when the organic group is an aryl group, the said ammonium salt is a primary amine salt, and mixtures of such salts, and provided that when said compound is other than an acid salt (said acid having a pK of 2.5 or less), no more than two of the groups R, $R^1$ and $R^2$ are —OH.

Included in the scope of said patent is NPMG mono isopropyl amine which is marketed by Monsanto Company under the trademark ROUNDUP ® and which is recognized today as one of the leading herbicides in the world.

As is noted from said patent which is based on U.S. applications filed in 1971 and published in 1974, e.g. U.S. Pat. No. 3,799,758, it was believed and claimed by said patentee that only very specific salt forming cations, i.e. those "wherein $R^6$ is a salt-forming cation selected from the groups consisting of cations of alkali metals, alkaline earth metals, copper, zinc, manganese, nickel, ammonium and organic ammonium selected from primary-, secondary- and tertiary-alkyl, alkenyl and alkynyl-amines, none of these having more than two amine groups; primary aryl amines, primary aryl diamines and heterocyclic amines and the acid addition salts of the above" were suitable for forming commercial phytotoxicant compositions.

This is also consistant with the possible salt forming groups defined by said patentee in such related patents as U.S. Pat. Nos. 3,455,675 and 3,556,762 dating back to applications filed in the 1960's and the tens of patents filed by the same patentee in the late 1970's.

Thus despite the widefelt need for herbicidal compositions comparable to ROUNDUP ® and the tens of patents relating to NPMG derivatives filed in the last years, since said 1974 patent no comparable NPMG derivative has been marketed.

According to the present invention there are now provided

N-Phosphonomethylglycine derivatives of the general formula I

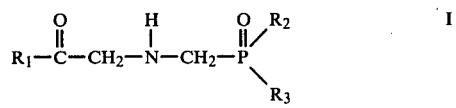

wherein $R_1$, $R_2$ and $R_3$ are independently selected from —OH and —$OR_4$ and $R_4$ is a salt-forming cation iminourea derivative of the general formula II

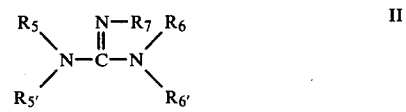

wherein $R_5$, $R_{5'}$, $R_6$, $R_{6'}$ and $R_7$ are independently

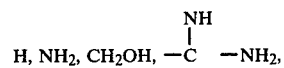

or an aryl, cycloalkyl or straight or branched chain alkyl or alkenyl group optionally substituted by hydroxy or halogen, or an alkylaryl group provided that
 (a) at least one but no more than two of $R_1$, $R_2$ or $R_3$ are $OR_4$,
 (b) no more than two $R_5$, $R_{5'}$, $R_6$, $R_{6'}$ are aryl or substituted aryl; and
 (c) no more than one of $R_5$, $R_{5'}$, $R_6$, $R_{6'}$ and $R_7$ is $CH_2OH$.

In the N-phosphonomethylglycine iminourea salts of the above formula preferably said alkyl and alkenyl groups contain up to 6 carbon atoms and chlorine is the halogen substituent.

Surprisingly, the novel iminourea salts of NPMG of the present invention are water soluble and exhibit comparable or even superior herbicidal activity when compared with the highly successful NPMG mono isopropyl amine and thus the present invention provides a whole new class of highly effective and needed herbicidal compositions.

It is believed that when one of the groups $R_1$, $R_2$, $R_3$ is $OR_4$, said group will be in the $R_2$ or $R_3$ position while when two of the groups are —$OR_4$ the first will be $R_1$ and the second will be $R_2$ or $R_3$.

The iminourea salt of the above formula are those prepared from low molecular weight iminourea, i.e. having a molecular weight below 400, such as: Guanidine, 2-Methylol Guanidine, 1-Amino Guanidine, 2-Methylol 1-Amino Guanidine, N,N'-Diaminoguanidine, Biguanide, 1-Methylguanidine, 1-3 Dimethylguanidine, 1-1-Dimethylguanidine, 1,1,3-Trimethylguanidine, 1,2,3-Trimethylguanidine, 1-Ethylguanidine, 1,3-Diethylguanidine, 1,1-Diethylguanidine, 1,1,3-Triethylguanidine, 1,2,3-Triethyguanidine, 1,1,3,3,-Tetramethylguanidine, 1,1,3,3-Tetraethylguanidine, pentamethyl guanidine, 1-Phenyl Guanidine, 1,3-Diphenyl Guanidine, 2-Methyol-1,3-Diphenyl Guanidine, 1,2,3-Triphenylguanidine, 1-Tolyl Guanidine, 1,3-Ditolyl Guanidine, 2-Methylol-1,3-DiPhenyl Guanidine, 1,2,3-Tritolyl Guanidine, 2-Napthyl Guanidine and 2-Anthryl Guanidine.

Preferred N-phosphonomethylglycine iminourea salts are those of the above formula wherein $R_5$, $R_{5'}$, $R_6$, $R_{6'}$ and $R_7$ are independently H, $NH_2$, phenyl, alkyl and tolyl.

Especially preferred compounds are those wherein the iminourea is guanidine, i.e., wherein $R_5$, $R_{5'}$, $R_6$, $R_{6'}$ and $R_7$ are all hydrogen; the iminourea is amino-guanidine, i.e., wherein one of $R_5$, $R_{5'}$, $R_6$, $R_{6'}$ is an amino group and the others are hydrogen, and diphenyl guanidine, i.e., wherein $R_5$ or $R_{5'}$ is phenyl or methyl-phenyl and the other is hydrogen or $R_6$ or $R_{6'}$ is phenyl or methylphenyl and the other is hydrogen.

Also preferred are compounds wherein one of $R_5$, $R_{5'}$, $R_6$ and $R_{6'}$ is an alkyl group and the rest are hydrogen.

The iminourea salts of NPMG of the present invention can be prepared by forming an admixture of the acid and the appropriate iminourea in water and heating the mixture until a clear solution is obtained. For the preparation of a herbicidal solution this clear solution, obtained as described above, can be used directly.

The compounds can be used individually, as admixtures of two or more compounds, or in admixture with an adjuvant. These compounds are effective as post-emergent phytotoxicants or herbicides and are characterized by broad spectrum activity, i.e. they control the growth of a wide variety of plants including but not limited to ferns, conifer (pine, fir and the like) aquatic, monocotyledona and dicotyledons.

The present invention also relates to a method of producing NPMG salt of iminourea. More particularly, this invention relates to the production of NPMG Salt of iminourea by the oxidation of N-(Phosphonomethyl) Iminodiacetic acid iminourea salt with an oxidizing agent such as hydrogen peroxide or a free oxygen containing gas with catalyst such as activated carbon or metal catalyst.

In Israel Patent 42393 there is described and claimed a process for the production of N-phosphonomethylglycine which comprises forming an admixture of N-(phosphonomethyl) iminodiacetic acid, water and an oxidizing agent and heating said admixture to a temperature at which said oxidizing agent and said N-(phosphonomethyl) iminodiacetic acid react to produce said N-phosphonomethyl glycine.

Similarly in Israel Patent 47202 there is described and claimed a process for the production of N-phosphonomethyl glycine which comprises contacting an aqueous solution of N-phosphonomethylimino diacetic acid with a molecular oxygen-containing gas at a temperature sufficiently elevated to initiate and sustain reaction and in the presence of a catalyst consisting essentially of activated carbon.

The novel compounds of the present invention can be prepared in a manner similar to that described in said patents.

Thus, in one aspect, the present invention also provides a process for preparing N-phosphonomethyl glycine imino urea salts as defined which comprises forming an admixture of water, an oxidizing agent and an N-(phosphonomethyl) iminodiacetic acid iminourea salt of the general formula III

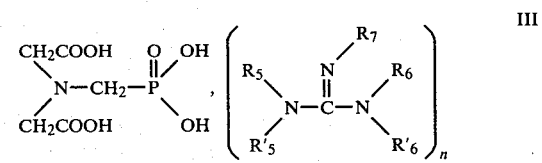

wherein $R_5$, $R_{5'}$, $R_6$, $R_{6'}$ and $R_7$ are as defined hereinbefore and n is 1 or 2 and heating said admixture to a temperature at which said oxidizing agent and said salt react to produce the salts of formula I as defined hereinbefore.

In a preferred process said oxidizing agent is a molecular oxygen containing gas and said reaction is carried out in the presence of a catalyst consisting essentially of activated charcoal.

Thus in accordance with said first above mentioned process N-(Phosphonomethyl) iminodiacetic acid iminourea salt having the formula:

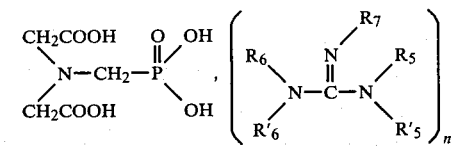

is mixed with water and heated to an elevated temperature. The oxidizing agent is then added and the iminodiacetic acid salt oxidatively converted into NPMG salt and other decomposition products. The NPMG salt is then isolated by precipitation, for example by addition of a water-miscible organic solvent, evaporation of water or cooling.

It is believed that the processes take place in accordance with the following equations,

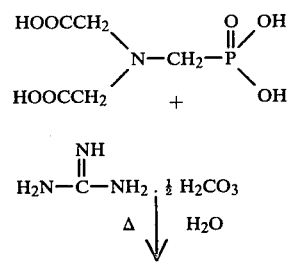

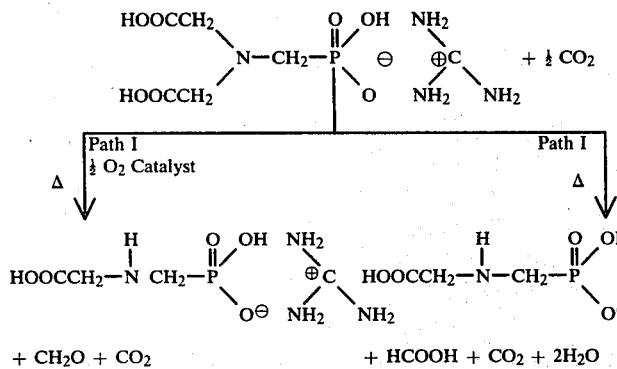

In conducting said processes the temperature of reaction can be from as low as 20° C. to 125° C. or even higher. It is preferred, for ease of reaction and to obtain the best yield of product, to conduct said processes at from about 70° C. to about 120° C.

The time of reaction is not narrowly critical and can vary from 15 minutes heating time to as high as 40 or more hours. Of course, it is obvious to those skilled in the art that the yield of the product will vary with the reaction time and the temperature of the reaction.

The process is carried out in an aqueous media. It is preferred to employ a saturated solution of N-(Phosphonomethyl) iminodiacetic salt in water. However, for ease of operation, the process is also operable at lower or higher concentration in water.

The ratio of reactants, that is the oxidizing agent and the N-(Phosphonomethyl) iminodiacetic acid (NPMIDA) salt is not narrow, as is apparent from the above equation. For best yields one should employ at least stoichiometric amount of oxidizing agent: 2 mole Hydrogen Peroxide (Path I) and ½ mole of $O_2$ (Path II) for each equivalent of N-(Phosphonomethyl) iminodiacetic salt. But in actual practice, to obtain the best yields, one employs 3-4 moles of Hydrogen Peroxide and ½ to 1 mole of oxygen for each mole NPMIDA salts. When a free oxygen-containing gas is employed it is preferred for convenience to conduct the process of this invention at a total pressure of from 0.5 kg/cm² to 200 kg/cm². It is even more preferred to conduct said process at pressure of from 1 kg/cm² to 5 kg/cm².

The manner in which the aqueous solution of the Iminodiacetic acid salts (NPMIDA) is contacted with the molecular oxygen containing gas and catalyst (activated carbon or metal catalyst) can vary greatly. For example the Iminodiacetic acid salts solution can be placed in a closed container with some free space containing molecular oxygen and shaken vigorously or agitated by stirring or molecular oxygen containing gas can be bubbled through said solution containing catalyst either through a straight tube or a tube with a fritted diffuser attached thereto. The contacting can also be accomplished in a tubular continuous reactor packed with activated carbon.

The Iminourea salts of N-(Phosphonomethyl) iminodiacetic acid are prepared by forming an admixture of the acid and the appropriate iminourea (or its carbonate salt) in water and heating the mixture until a clear solution is obtained. The Iminourea undergoes protonation on the imine nitrogen (R—N=C<) thus yielding a cation that can be regarded as a resonance hybrid of three energetically equivalent structure.

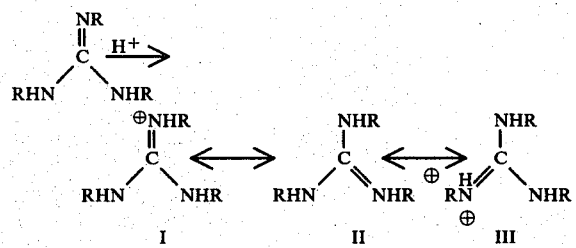

The resonance stabilization energy of the above cation serve as the driving force to promote the reaction of Iminourea derivatives (an amide) with N-(Phosphonomethyl) Iminodiacetic acid and N-Phosphonomethyl glycine which both are acid.

The oxidizing agent which can be employed to prepare the compounds of the present invention include oxidizing agents such as inorganic peroxides, including Hydrogen peroxide and organic peroxides. The organic peroxide oxidizing agents include: Performic acid, Peracetic acid, Perbenzoic acid and the like. Other inorganic oxidizing agents include oxygen, air, oxygen diluted with helium, argon, nitrogen or other inert gas in the presence of catalysts such as: activated carbon, metallic catalysts (Pt, Pd, Rh, Ru, etc.) alone or on activated supports such as activated charcoal, aluminium oxide, asbestos etc.

The activated carbon catalysts employed are characterized by high adsorptive capacity for gases, vapors and colloidal solids and relatively high specific surface areas. The specific surface area of the activated carbon can be from 100-2000 square meters per gram. It is preferred to employ activated carbons having a specific surface area of 400 to 1600 square meters per gram.

The activated carbons employed in said process can be in the form of powders or granules. In the powder form the activated carbons consist largely of material having a particle size finer than 325 mesh although some larger particles may also be present in the granular form. The particle size range can vary considerably, particle size of 4×10 mesh, 8×30 mesh and 20×30 mesh can be used.

The amount of granular or powdered activated carbon employed in this process can range from 0.5 to 100 or more parts by weight for every 100 parts by weight of NPMIDA salt employed.

As is apparent from the experiments, the form of the activated carbon, its PH and its area, all effect the rate of the reaction of the NPMIDA salts with oxygen in this process. The experiments indicate that the reaction rate is faster when the active carbon was washed with concentrated hydrochloric acid and then with water (up to PH=7) before use.

Some example of activated carbon are: Norit PN-4, Norit A, Norit ACX (Amer. Norit Co., INc., Jacksonville Fla.), Darco 6-60 (ICI-America), grade 235 and 256 (Witco Chemical Corp), Columbia SXAC (Union Carbide) and the like.

The metal on support catalyst are the commercial 5% metal on activated carbon such as 5% Pd/c, 5% Rh/c, 5% Pt/c, 5% Pt/Al$_2$O$_3$ and 5% Rh/Al$_2$O$_3$.

The organic solvent which is employed in the isolation of the product of this invention is one of the water-miscible organic solvents and may include alcohols such as methanol, ethanol, isopropanol, butanol and the like; Ketones such as acetone, methylethyl Ketone and the like: glycols and polyglycols, for example ethylene glycol, propylene glycol and the like. Many other water-miscible organic solvents that can be employed in isolating the product will be apparent to those skilled in the art.

While the invention will now be described in connection with certain preferred embodiments in the following examples it will be understood that it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars described are by way of example and for purposes of illustrative discussion of preferred embodiments of the present invention only and are presented in the cause of providing what is believed to be the most useful and readily understood description of procedures as well as of the principles and conceptual aspects of the invention.

In the examples, all parts, percentages and properties are by weight unless otherwise indicated.

EXAMPLE 1

A mixture of about 34 parts (0.2 mole) NPMG, 100 parts of water and 27.2 (0.2 mole) 1-Aminoguanidine bicarbonate was agitated in a suitable reaction vessel at 30° C. After dissolution was complete as indicated by clarification of the reaction mixture and the ceasing of evolution of carbon dioxide, the reaction mixture was concentrated on a steam bath at reduced pressure. The residue was washed with hot isopropanol and dried (90° C./30 mm Hg) the product thus obtained is the monoamino Guanidine Salt as a very deliquest white solid. m.p.—80° (dec.) (yield=95%) NMR (D$_2$O, δppm), relative to HOD): −1.17 (S, 2H); −1.64 (d, 2H, J=13 H$_z$).

Elementary analysis: calculated for C$_4$H$_{14}$N$_5$O$_5$P: C, 19.75; H, 5.76% found: C, 19.53: H, 5.52% Following the above procedure, other Guanidine salts of NPMG can be prepared, e.g. the Mono Guanidine Salt white solid, m.p—218°-220° (dec.), N,N Diaminoguanidine salt, mono biguanidine salt, di-(aminoguanidine)salt and di-(guanidine)salt (white solid).

EXAMPLE 2

A mixture of about 34 parts (0.2 mole) NPMG, 150 parts water and 23.0 (0.2 mole) 1,1,3,3-Tetramethyl-guanidine was agitated in a suitable vessel at 30°. After dissolution was complete the solution was filtered and concentrated on a steam bath at reduced pressure. The residue was washed with hot isopropanol and dried (90°/30 mm H). The produce thus obtained is the mono-tetramethyl guanidine salt as a white deliquest solid m.p. 175°-6° C. (dec.) (yield—90%). NMR (D$_2$O, δppm, relative to HOD): −1.23 (S, 2H): −1.73 (d, 2H, J=13 H$_z$): −2.03 (S, 12H, CH$_3$). Following the above procedure other Guanidine salts of NPMG can be prepared e.g. the Methyl Guanidine Salt, the 1,3-Di Methyl Guanidine Salt, 1,1-dimethyl guanidine salt, the Ethyl Guanidine Salt, the 1,3 Di-Ethyl Guanidine Salts, 1,1-Di ethyl Guanidine Salt, the 1,1,3,3 Tetra Ethyl Guanidine Salt, 1,1,3-Trimethyl Guanidine Salt, 1,2,3 Tri Methyl Guanidine Salt, 1,1,3 Tri Ethyl Guanidine salt, 1,2,3 Triethyl Guanidine Salt, the pentamethyl guanidine salt, the di-(tetramethyl guanidine)salt, the di-(1,1,-diethyl guanidine) salt, the cyclohexylguanidine salt, the 1-cyclopentylguanidine salt, the 1-chloromethyl guanidine salt, the 1-chloroethyl guanidine salt, and 1-hydroxymethyl guanidine salt.

EXAMPLE 3

A mixture of 34 parts (0.2 mole) of NPMG, 200 parts of water and 43.6 (0.2 mole) 1,3-Diphenyl Guanidine was agitated in a suitable vessel at 30° for 30 minutes. The solution was filtered to remove a small amount of sediment. The clear filtrate was then concentrated at reduced pressure, washed with hot isopropanol and dried (90°/30 mm H) yielding a white solid. The product was identified as the Mono-Diphenyl Guanidine salt of NPMG. m.p. 124° (dec.) (yield: 85%) NMR (D$_2$O, δppm, relative to HOD): +2.32 (S, 10H, aromatic); −1.33 (S, 2H); −1.83 (d, 2H, J=13 H$_z$). Following the above procedure other salts of NPMG can be prepared e.g., 1-Phenyl Guanidine Salt, di-(1,3-diphenyl guanidine) salt, 1,2,3-Triphenyl Guanidine salt, 1,1-Diphenyl Guanidine salt, 1-benzyl guanidine salt, 1-(4-methyl)-benzyl guanidine salt, 1-alkyl guanidine salt, 1-butenyl guanidine salt and 1-pentenyl guanidine salt.

EXAMPLE 4

A mixture of 34 parts (0.2 mole) NPMG 200 parts of water and 49.5 (0.2 mole) of 1,3-Di-o-Tolylguanidine was heated at 30° C. for 30 minutes. The clear solution was then filtered with Norit® and concentrated at reduced pressure, washed with hot isopropanol and dried (90° C., 30 mm Hg). The product thus obtained is the Mono 1,3-Di-O-Tolylguanidine Salt as a white deliquest solid m.p. 203 (dec.) yield: 87%). NMR (D$_2$O, δppm, relative to HOD): −2.56 (S, 8H, aromatic); −1.1 (S, 2H); −1.6 (d, 2H, J=13 Hz), −2.48 (S, 6H, CH$_3$). Following the above procedure other salts of NPMG can be prepared e.g. 1-tolyguanidine salt, 1,3-Di-p-Tolyguanidine salt, 1,2,3 Tritolylguanidine salt, 1,1-Di Tolyguanidine salt, 1-Chlorophenyl guanidine salt, 1,3-dichlorophenyl guanidine salt and di-(1,3-di-o-tolyl-guanidine) salt.

| SOLUBILITY OF NPMG-IMINOUREA SALTS | | |
|---|---|---|
| NPMG Salt | Weight dissolved in 100 ml water at 20° C. (in grams) | NPMG equivalent |
| Guanidine: | 15.7 | 11.6 |
| Di-(guanidine) | ~300 | ~195 |
| Aminoguanidine | ~300 | ~208 |
| 1,1,3,3 Tetra Methyl Guanidine | 165 | 98.0 |
| 1,3 Diphenyl Guanidine | ~200 | ~88.9 |

-continued

| ROMAN NUMERAL | COMPOUND NAME |
| --- | --- |
| I | NPMG MONO (GUANIDINE) SALT |
| II | NPMG MONO (AMINOGUANIDINE) SALT |
| III | NPMG MONO (DIPHENYL GUANIDINE) SALT |
| IV | NPMG MONO (DI-O-TOLYL GUANIDINE) SALT |
| V | NPMG MONO (TETRA METHYL GUANIDINE) SALT |
| VI | NPMG MONO (METHYL GUANIDINE) SALT |
| VII | NPMG MONO (1,1-DI METHYL GUANIDINE) SALT |
| VIII | NPMG MONO (1,1-DI ETHYL GUANIDINE) |
| IX | NPMG DI-(GUANIDINE) SALT |
| X | NPMG MONO ISOPROPYL AMINE SALT (ROUND UP(R) ISRAEL PATENT 37993) |

| SOLUBILITY OF NPMG-IMINOUREA SALTS | | |
| --- | --- | --- |
| NPMG Salt | Weight dissolved in 100 ml water at 20° C. (in grams) | NPMG equivalent |
| 1,3-Di-O—Tolyl Guanidine | ~175 | ~72.5 |

COMPARATIVE EXAMPLE 5

The post-emergence herbicidal activity of various compounds of this invention is demonstrated as follows: The active ingredients are applied in spray to 21 day old specimens of various plant species. The spray, a water or organic solvent-water solution containing active ingredient and a surfactant (75 parts cationic detergent and 25 parts of nonionic one), is applied to the plants in different sets of pans at several rates (kilogram per dunam) of active ingredient. The treated plants are placed in a green-house and the effects are observed and recorded after approximately 2 weeks as is indicated in Table 1. The post-emergence herbicidal activity index used in Table 1 is as follows:

| PLANT RESPONSE | INDEX | PLANT RESPONSE | INDEX |
| --- | --- | --- | --- |
| No injury | 0 | Severe injury | 3 |
| Slight injury | 1 | Killed | 4 |
| Moderate injury | 2 | | |

The plant species utilized in these tests are identified by letter in accordance with the following legend:

As can be seen from the above table all of the above tested compounds of the present invention exhibit herbicidal properties comparable to that of Roundup ®.

Furthermore, it has been found that the compounds of the present invention exhibit superior drift properties, i.e, have a lesser tendency to drift after application than does Roundup ®. Preferred methods of producing the compounds of the present invention are illustratively described in the following examples.

EXAMPLE 6

A series of runs were made to oxidize N-(Phosphonomethyl)imino diacetic salt using $H_2O_2$ as oxidant.

Forty parts of water and 0.02 mole of NPMIDA salt were charged into a suitable reactor. The mixture was heated to 80° C. and then 8.8 parts of 30% $H_2O_2$ was added over a period of 1 to 2 hours while maintaining the temperature at 70° C. The reaction was then heated at 80° C. with stirring until Nuclear Magnetic Resonance spectral analysis showed that the reaction was essentially complete. The reaction was terminated, excess $H_2O_2$ was decomposed by activated carbon, the carbon was filtered off and the filtrate was diluted with excess ethanol. The precipitated was collected, washed with ether and dried yielding a white solid. The solid product was analyzed by N.M.R. and IR spectral analysis. The NPMG acid can be isolated from the salt by addition of concentrated hydrochloric acid to the reaction solution. This acid was also analyzed by NMR spectral analysis. Table II gives the result of these experiments.

TABLE I

| A. Paspelon Paspoloides | K. Lygeum Spartum |
| --- | --- |
| B. Chloris Gayana | L. Panicum Repens |
| C. Phalaris Paradoxa | M. Cynodon Dactylon |
| D. Rubus Conesenes | N. Sorghum Halepense |
| E. Eragrostis Bipinnata | O. Convolvulus Arvensis |
| F. Imperota Cylindrica | P. Polygonnum Eqviseliforme |
| G. Andropogone Hirtum | |
| H. Cyperus Rotundus | |
| I. Inula Viscosa | |
| J. Phrogmites Communis | |

| COMPOUND | A | B | C | D | E | F | G | H | I | J | K | L | M | N | O | P |
| --- | --- | --- | --- | --- | --- | --- | --- | --- | --- | --- | --- | --- | --- | --- | --- | --- |
| I | 2 | 2 | 2 | 1 | 1 | 2 | 3 | 3 | 2 | 1 | 1 | 2 | 2 | 2 | 3 | 3 |
| II | 3 | 3 | 2 | 2 | 1 | 3 | 3 | 3 | 3 | 1 | 2 | 3 | 2 | 2 | 3 | 3 |
| III | 2 | 2 | 2 | 1 | 1 | 3 | 3 | 3 | 3 | 1 | 1 | 3 | 2 | 2 | 3 | 3 |
| IV | 3 | 2 | 2 | 1 | 2 | 3 | 2 | 3 | 3 | 1 | 1 | 2 | 2 | 2 | 3 | 3 |
| V | 2 | 2 | 1 | 1 | 1 | 3 | 3 | 2 | 2 | 1 | 1 | 2 | 1 | 2 | 3 | 2 |
| VI | 2 | 2 | 2 | 1 | 2 | 2 | 3 | 3 | 2 | 1 | 1 | 2 | 2 | 2 | 3 | 3 |
| VII | 2 | 1 | 2 | 1 | 1 | 3 | 2 | 3 | 2 | 1 | 1 | 2 | 1 | 2 | 3 | 2 |
| VIII | 2 | 2 | 1 | 1 | 1 | 3 | 2 | 3 | 3 | 2 | 1 | 2 | 2 | 2 | 2 | 2 |
| IX | 2 | 3 | 3 | 1 | 1 | 3 | 3 | 4 | 3 | 2 | 2 | 3 | 2 | 2 | 3 | 4 |
| X | 2 | 2 | 2 | 1 | 1 | 3 | 3 | 3 | 3 | 1 | 1 | 2 | 2 | 2 | 3 | 3 |

TABLE II

| Experiment No. | Iminourea | Reaction time (h) | Mole % NPMG salt | Mole % NPMIDA salt |
|---|---|---|---|---|
| 1 | G | 4 | 98 | 2 |
| 2 | *AG | 4 | 98 | 2 |
| 3 | DPG | 4 | 100 | 0 |
| 4 | DPG | 4.5 | 100 | 0 |
| 5 | DTG | 4.5 | 97 | 3 |
| 6 | TMG | 3.5 | 97 | 3 |
| 7 | MG | 3.0 | 98 | 2 |

G. Guanidine
DTG. Ditolyl Guanidine
AG. Aminoguanidine
TMG. Tetramethylguanidine
MG. Methylguanidine
DPG. Diphenylguanidine
*Some of the aminoguanidine was oxidized to nitroguanidine and nitrosoguanidine during the oxidation.

EXAMPLE 7

A series of runs were made to oxidize N-(Phosphonomethyl)iminodiacetic salt using oxygen as oxidant. This series was conducted in a low pressure apparatus consisting of a Parr Shaker to provide agitation. Table III gives the result of these experiments. In these experiments 0.5–1 grams (g) of catalyst, 0.02 mole of Iminodiacetic salt and 50 g. of distilled water were charged into the bottle and heated to 85° C. on a hot plate and the heating shield heated to 90° C. The bottle was sealed, placed in the shield and alternately pressurized and depressurized several times with $O_2$ gas at 1–3 Kg/cm$^2$ to remove the air. The reactions were all conducted at 3–1 kg/cm$^2$ with discharge and repressurization to ensure sufficient oxygen being present. In the reaction that was conducted at 1 kg/cm$^2$ the oxygen was bubbled through said solution through a tube with a fritted diffuser attached thereto. After the reaction was terminated, the catalyst was filtered off and the filtrate evaporated under reduced pressure which yielded a solid product. The solid product was analyzed by N.M.R and I.R spectral analysis. The NPMG acid can be isolated from the salt by addition of concentrated hydrochloric acid to the reaction solution. This acid was also analyzed by N.M.R. Spectral analysis.

The compositions of this invention provide a wide spectrum of weed control and are also extremely useful as general herbicides as well as in controlling unwanted plants in orchards, tree farms, and various crops. For example, it has been found that by directing a spray of the compositions of this invention at the unwanted plants while essentially preventing such spray from contacting the leaves of trees, that such unwanted plants are controlled while there is no apparent injury to the trees. In such directed spraying, the spray can fall on the woody portion of the fruit tree or other tree without any apparent effect. Thus, the directed spray method of control is useful with crops such as plantation crops, i.e., rubber, coffee, bananas, tea, etc. and in orchards such as citrus fruits, apples, peaches, pears, nuts, olive, in vineyards and in bramble crops and in nursery crops to control the undesired plants; and in crops such as cotton, soybeans, sugarcane and the like.

The compositions of this invention are also useful for control of weeds between cropping seasons, for the renovation of stale seed beds and the like.

In applying the compositions of this invention to the plants which it is desired to control, it has been found to be desirable that the plant be emerged from the ground and even more desirable, that the plant be at least at the 2 leaf stage for maximum effect.

It has been found that when the plants to be controlled have a portion of their growth above the ground or water, and the above-ground or above-water portion of the plant contacted with the herbicidal compositions of this invention at appropriate rates, the herbicide is translocated to kill such plant parts which are below the ground or water surface.

One can obtain limited selectivity in crops such as cotton, soybeans, sugar cane and like crops by directing the spraying of a composition of this invention at a selected concentration on vegetation around the base of such plants with minimal spray contact with the leafy portions of such crop plants. The directed spraying can be done with or without a protective device to prevent contact of the spray with the leaves of such crop plants.

A non-exhaustive list of some of the plant species which are controlled by the compositions of this invention, in addition to those shown in Table I, are set forth below:

TABLE III

| Experiment No. | Iminourea | Catalyst (g) | Pressure Kg/cm$^2$ | Reaction time (h) | Mole % NPMG Salt | Mole % NPMIDA Salt |
|---|---|---|---|---|---|---|
| 8 | G | Norit PN-3; 0.5 g | 1 | 10 | 98 | 2 |
| 9 | G | " | 2.3 | 2 | 100 | 0 |
| 10 | G | 5% Pt/C; 0.5 g | 2 | 2.5 | 95 | 5 |
| 11 | G | Norit A; 0.5 g | 2 | 1.5 | 90 | 10 |
| 12 | *AG | 5% Pt/C; 1.0 g | 1 | 12 | 100 | 0 |
| 13 | *AG | Norit PN-3; 0.5 g | 1 | 12 | 100 | 0 |
| 14 | *AG | 5% Pt/Al$_2$O$_3$; 0.5 g | 2.2 | 3 | 98 | 0 |
| 15 | DPG | Norit PN-3; 1.0 g | 1 | 10 | 100 | 0 |
| 16 | DPG | Norit Acx; 1.0 g | 1 | 12 | 95 | 5 |
| 17 | DPG | 5% Rh/C; 1.0 g | 2 | 4 | 100 | 0 |
| 18 | DTG | Norit PN-3; 1.0 g | 1 | 10 | 95 | 5 |
| 19 | DTG | Norit A; 1.0 g | 2.1 | 2 | 90 | 10 |
| 20 | TMG | Norit PN-3; 0.5 g | 1 | 10 | 100 | 0 |
| 21 | TMG | Norit A; 0.5 g | 2 | 3 | 100 | 0 |
| 22 | MG | Norit PN-3; 0.5 g | 1 | 11 | 100 | 0 |
| 23 | MG | 5% Pd/C; 0.5 g | 2 | 2 | 95 | 5 |

*Some of the aminoguanidine was oxidized to nitrosoguanidine and nitroguanidine during the oxidation.

| | |
|---|---|
| CRAMBE HISPANICA | EUPHORIA CYBIRENSIS |
| ERUCARIA MYAGROIDES | CROZOPHORA TINCTORIA |
| HIRCHFELDIA INCANA | ERODIUM MOSCHATUM |

-continued

| | |
|---|---|
| DIPLOTAXIS ERUCOIDES | RANUNCULUS TRACHYCARFUS |
| AMARANTHUS RETROFLEXUS L | RANUNCULUS ARVENSIS |
| AMARANTHUS LIVIDUS L | SOLANUM ELEAGNIFOLIUM |
| AMARANTHUS ALBUS L | POLYGONIUM EQUISELIFORME |
| AMARANTHUS GRAECIZANS | ANTHEMIS PSEUDOCOTULA |
| ECHINOCHLOA COLONUM | ANTHEMIS MELANOLEPIS |
| CYNODON DACTYLON | CARTHAMUS TENUIS |
| PHALARIS | ORMENIS MIXTA |
| LOLIUM RIGIDUM | EROGERON CRISPUS |
| CHENOPODIUM MURALE | SCORPIURUS MURICATA |
| BETA VULGARIS | HYMENOCARPUS CIRCINNATUS |
| CHENOPODIUM OPULIFOLIUM | SECURIGERA SECURIDACA |
| SONCHUS OLERACEUS | DIGITARIA SANGUINALIS |
| XANTHIUM STRUMARIUM | SORGHUM HALEPENSE |
| CALENDULA ARVENSIS | SETARIA VERTICILLATA |
| RIDULFIA SEGETUM | AVENA STERILIS |
| TORDYLIUM AEGYPTIACUM | AMMI MAJOR |
| BUPLEVRUM PERFOLIATUM | CONVOLVULVUS ARVENSIS |
| VICIA VULGARE | |

The phytotoxicant compositions, including concentrates which require dilution prior to application to the plants, of this invention contain at least one active ingredient and an adjuvant in liquid or solid form. The compositions are prepared by admixing the active ingredient with an adjuvant including diluents, extenders, carriers and conditioning agents known per se to provide compositions in the form of finely-divided particulate solids, pellets, solutions, dispersions or emulsions. Thus the active ingredient can be used with an adjuvant such as a finely-divided solid, a liquid or organic origin, water, a wetting agent, a dispersing agent, an emulsifying agent or any suitable combination of these. From the viewpoint of economy and convenience, water is the preferred diluent, particularly with the highly water-soluble guanidine salts such as the Aminoguanidine salt and Di-aryl guanidine salts. With these derivatives, solutions containing as high as 60% by weight of active materials can be readily prepared.

The phytotoxicant compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent" it is understood that wetting agents, dispersing agents, suspending agents and emulsifying agents are included therein. Anionic, cationic and nonionic agents can be used with equal facility.

Preferred wetting agents are alkyl benzene sulfated fatty alcohols, amines or acid amides, sulfated or sulfonated fatty acid esters petroleum sulfonates, sulfonated vegetable oils, polyoxyethylene derivatives of alkylphonols (particularly isooctylphenol and nonylphenol), Mono-fatty di-alkyl amine oxide, and mono-fatty di-alkyl benzalkonium chloride.

Preferred dispersants are methyl cellulose, polyvinyl alcohol, sodium lignin sulfonates, polymeric alkyl naphthalene sulfonates and sodium naphthalene sulfonate.

Water-dispersible powder compositions can be made containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, and synthetic magnesium silicate. The water-dispersible compositions of this invention usually contain from about 10 to about 90 parts by weight of active ingredient, from about 0.5 to 20 parts by weight of wetting agent, from about 0.5 to 20 parts by weight of dispersant and from 5.0 to about 90 parts by weight of inert, solid extender, all parts being by weight of the total composition.

Aqueous suspensions can be prepared by mixing together and grinding an aqueous slurry of water-insoluble active ingredient in the presence of dispersing agents to obtain a concentrated slurry of very finely-divided particles. The resulting concentrated aqueous suspension is characterized by its extremely small particle size, so that when diluted and sprayed, coverage is very uniform.

Emulsifiable oils are usually solutions of active ingredient in water-immiscible or partially water-immiscible solvents together with a surface active agent. Suitable solvents for the active ingredient of this invention include hydrocarbons and water-immiscible ethers, esters or ketones. The emulsifiable oil compositions generally contain from about 10 to 95 parts active ingredient, about 2 to 50 parts surface active agent and about 4 to 90 parts solvent, all parts being by weight based on the total weight of emulsifiable oil.

Although compositions of this invention can also contain other additives, for example fertilizers, phytotoxicants and plant growth regulants, pesticides and the like used as adjuvants or in combination with any of the above-described adjuvants, it is preferred to employ the compositions of this invention, alone with sequential treatments with the other phytotoxicants, fertilizers and the like for maximum effect. For example, the field could be sprayed with a composition of this invention either before or after being treated with fertilizers, other phytotoxicants and the like. The compositions of this invention can also be admixed with the other materials, e.g. fertilizers, other phytotoxicants, etc., and applied in a single application. Chemicals used in combination with the active ingredients of this invention either simultaneously or sequentially include for example triazines, ureas, carbamates, acetamides, acentanilides, uracils, acetic acids, phenols thiolcarbamates, triazoles, benzoic acids, nitriles and the like such as:
3-amino-2,5-dichlorobenzoic acid
3-amino-1,2,4-triazole
2-methoxy-4-ethylamino-6-isopropylamino-s-triazine
2-chloro-4-ethylamino-6-isopropylamino-2-triazine
2-chloro-N,N-diallylacetamide
2-chloroallyl diethyldithiocarbamate
N'-(4-chlorophenoxy)phenyl-N,N-dimethylurea
1,1'-dimethyl-4,4'-bipyridinium dichloride isopropyl m-(3-chlorophenyl)carbamate
2,2-dichloropropionic acid
S-2,3-dichloroallyl N,N-diisopropylthiolcarbamate
2-methoxy-3,6-dichlorobenzoic acid
2,6-dichlorobenzonitrile
N,N-dimethyl-2,2-diphenylacetamide
6,7-dihydrodipyrido(1,2-a:2',1'-c)-pyrazidiinium salt
3-(3,4-dichlorophenyl)-1,1-dimethylurea
4,6-dinitro-o-sec-butylphenol
2-methyl-4,6-dinitrophenol
ethyl N,N-dipropylthiolcarbamate
2,3,6-trichlorophenylacetic acid
5-bromo-3-isopropyl-6-methyluracil
3-(3,4-dichlorophenyl)-1-methoxy-1-methylurea
2-methyl-4-chlorophenoxyacetic acid
3-(p-chlorophenyl)-1,1-dimethylurea
1-butyl-3-(3,4-dichlorophenyl)-1-methylurea
N-1-naphthylphthalamic acid
1,1'-dimethyl-4-4' bipyridinium salt
2-chloro-4-6-bis(isopropylamino)-s-triazine
2-chloro-4,6-bis(ethylamino)-s-triazine
2,4-dichlorophenyl-4-nitrophenyl ether
alpha, alpha, alpha-trifluoro-2,6-dinitro-N,N-dipropyl-p-toluidine
S-propyl dipropylthiolcarbamate
2,4-dichlorophenoxyacetic acid
N-isopropyl-2-chloroacetanilide
2',6'-diethyl-N-methoxymethyl-2-chloroacetanilide
monosodium acid methanearsonate
disodium methanecarsonate
N-(1,1-dimethylpropynyl)-3,5-dichlorobenzamide Fertilizers useful in combination with the active ingredients include for example ammonium nitrate, urea, potash and superphosphate.

The application of an effective amount of the compounds of this invention to the plant is essential and critical for the practice of the present invention. The exact amount of active ingredient to be employed is dependent upon the response desired in the plant as well as such other factors as the plant species and stage of development thereof, and the amount of rainfall as well as the specific glycine employed. In foliar treatment for the control of vegetative growth, the active ingredients are applied in amounts from about 0.1 to about 50 or more kilogram per dunam. In applications for the control of aquatic plants, the active ingredients are applied in amounts of from about 0.1 parts per million to about 2000 parts per million, based on the aquatic medium. An effective amount for phytotoxicant or herbicidal control is aquatic medium. An effective amount for phytotoxicant or herbicidal control is that amount necessary for overall or selective control, i.e., a phytotoxic or herbicidal amount. It is believed that one skilled in the art can readily determine from the teachings of this specification, including examples, the approximate application rate.

The compositions of this invention are also useful as harvesting aids in many crops. Thus, for example, the crop could be sprayed with the compositions of this invention to reduce the bulk of unwanted material and make the harvesting of the crops easier. Such crops are, for example, peanuts, soybeans, and root crops such as potatoes, sugar beets, red beets, and the like.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come with the meaning and range of equivalency of the claims are therefore intended to be embraced therein.

What is claimed is:

1. N-Phosphonomethylglycine derivatives of the general formula I

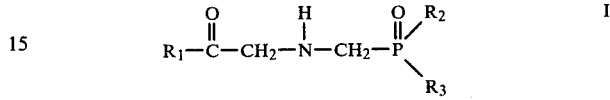

wherein $R_1$, $R_2$ and $R_3$ are independently selected from —OH and —$OR_4$ wherein $R_4$ is a salt forming cation iminourea derivative of the general formula II

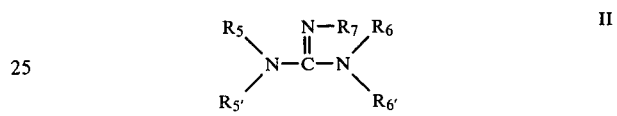

wherein $R_5$, $R_{5'}$, $R_6$, $R_{6'}$ and $R_7$ are independently

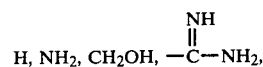

H, $NH_2$, $CH_2OH$, —C—$NH_2$, or an aryl, cycloalkyl or straight or branched chain alkyl or alkenyl group optionally substituted by hydroxy or halogen, or an alkylaryl group, provided that (a) at least one but no more than two of $R_1$, $R_2$ or $R_3$ are $OR_4$, (b) no more than two $R_5$, $R_{5'}$, $R_6$, $R_{6'}$ are aryl or substituted aryl; and (c) no more than one of $R_5$, $R_{5'}$, $R_6$, $R_{6'}$ and $R_7$ is $CH_2OH$.

2. N-Phosphonomethylglycine iminourea salts according to claim 1 wherein $R_5$, $R_{5'}$, $R_6$, $R_{6'}$ and $R_7$ are independently selected from H, $NH_2$, phenyl, alkyl and tolyl.

3. N-Phosphonomethylglycine iminourea salts according to claim 1 wherein $R_5$, $R_{5'}$, $R_6$, $R_{6'}$ and $R_7$ are all hydrogen.

4. N-Phosphonomethylglycine iminourea salts according to claim 1 wherein one of $R_5$, $R_{5'}$, $R_6$, $R_{6'}$ is an amino group and the others are hydrogen.

5. N-Phosphonomethylglycine iminourea salts according to claim 1 selected from the group wherein $R_5$ or $R_{5'}$ is phenyl or methylphenyl and the other is hydrogen or $R_6$ or $R_{6'}$ is phenyl or methylphenyl and the other is hydrogen.

6. N-Phosphonomethylglycine derivatives according to claim 1 wherein $R_1$ and $R_2$ are $OR_4$ and $R_3$ is hydroxy.

7. N-Phosphonomethylglycine derivatives according to claim 1 wherein $R_2$ is $OR_4$ and $R_1$ and $R_3$ are hydroxy.

8. N-Phosphonomethylglycine derivatives according to claim 1 wherein one of $R_5$, $R_{5'}$, $R_6$ and $R_{6'}$ is an alkyl group and the rest are hydrogen.

9. N-Phosphonomethylglycine derivatives according to claim 1 wherein said alkyl and alkenyl groups contain up to 6 carbon atoms.

10. N-Phosphonomethylglycine derivatives according to claim 1 wherein said halogen is chlorine.

11. A phytotoxic composition comprising an adjuvant and an effective amount of one or more N-phosphonomethylglycine iminourea salts as claimed in claim 1.

12. A method of controlling vegetation comprising applying a phytotoxic amount of a compound as claimed in claim 1.

* * * * *